United States Patent [19]
Eaton et al.

[11] 3,996,124
[45] Dec. 7, 1976

[54] FLUSH MOUNTED CORROSION PROBE ASSEMBLY FOR PIPELINE

[75] Inventors: Paul E. Eaton, Cedar Hill; Robert R. Annand, St. Louis, both of Mo.

[73] Assignee: Petrolite Corporation

[22] Filed: July 30, 1975

[21] Appl. No.: 600,671

[52] U.S. Cl. .................... 204/195 C; 324/65 CR; 73/86

[51] Int. Cl.² .................. G01N 27/46; G01N 27/30

[58] Field of Search ............ 204/1 C, 195 C, 280, 204/286; 324/29, 65 CR, 71 R; 23/253 C

[56] References Cited

UNITED STATES PATENTS

| | | | |
|---|---|---|---|
| 3,166,485 | 1/1965 | Lloyd | 204/195 C X |
| 3,491,012 | 1/1970 | Winslow, Jr. | 204/195 C |
| 3,632,495 | 1/1972 | Watson et al. | 204/195 C |
| 3,748,247 | 7/1973 | Weisstuch | 204/195 C |
| 3,846,795 | 11/1974 | Jones | 340/421 |
| 3,910,830 | 10/1975 | Mayse | 204/195 C |

OTHER PUBLICATIONS

M-535 Probe and Cosasco Fitting Assembly, pp. 402.1 and 507.0 of T. D. Williamson, Inc. Catalog, Tulsa, Okla., (1971), Cosasco (Grant Tool Co.), Catalog 73-1, (1973).

Primary Examiner—G. L. Kaplan
Assistant Examiner—Aaron Weisstuch
Attorney, Agent, or Firm—Emil J. Bednar

[57] ABSTRACT

A flush mounted probe assembly for monitoring the corrosion environment within a thin boundary liquid film disposed along the interior sidewall surface of a pipeline carrying fluids. The assembly comprises a probe received within a nipple secured to the pipeline. An end portion of the probe projects snugly into the opening and terminates in an end face residing substantially in alignment with the interior sidewall surface. The probe is releasably secured within the nipple and sealed thereto against fluid leakage. The probe's end face has an imperforate smooth surface which is contoured and dimensioned within the opening in the pipeline to substantially conform to the interior sidewall surface without a surface discontinuity in the pipeline to disrupt the thin boundary liquid film. The probe carries electrodes having smooth exposed surfaces merging into the end face. Electrical conductors connect with the electrodes in the probe and extend in electrical isolation to an external circuit connection. In a preferred embodiment, the end portion is circular with a planar end face containing annular metal electrodes.

3 Claims, 6 Drawing Figures

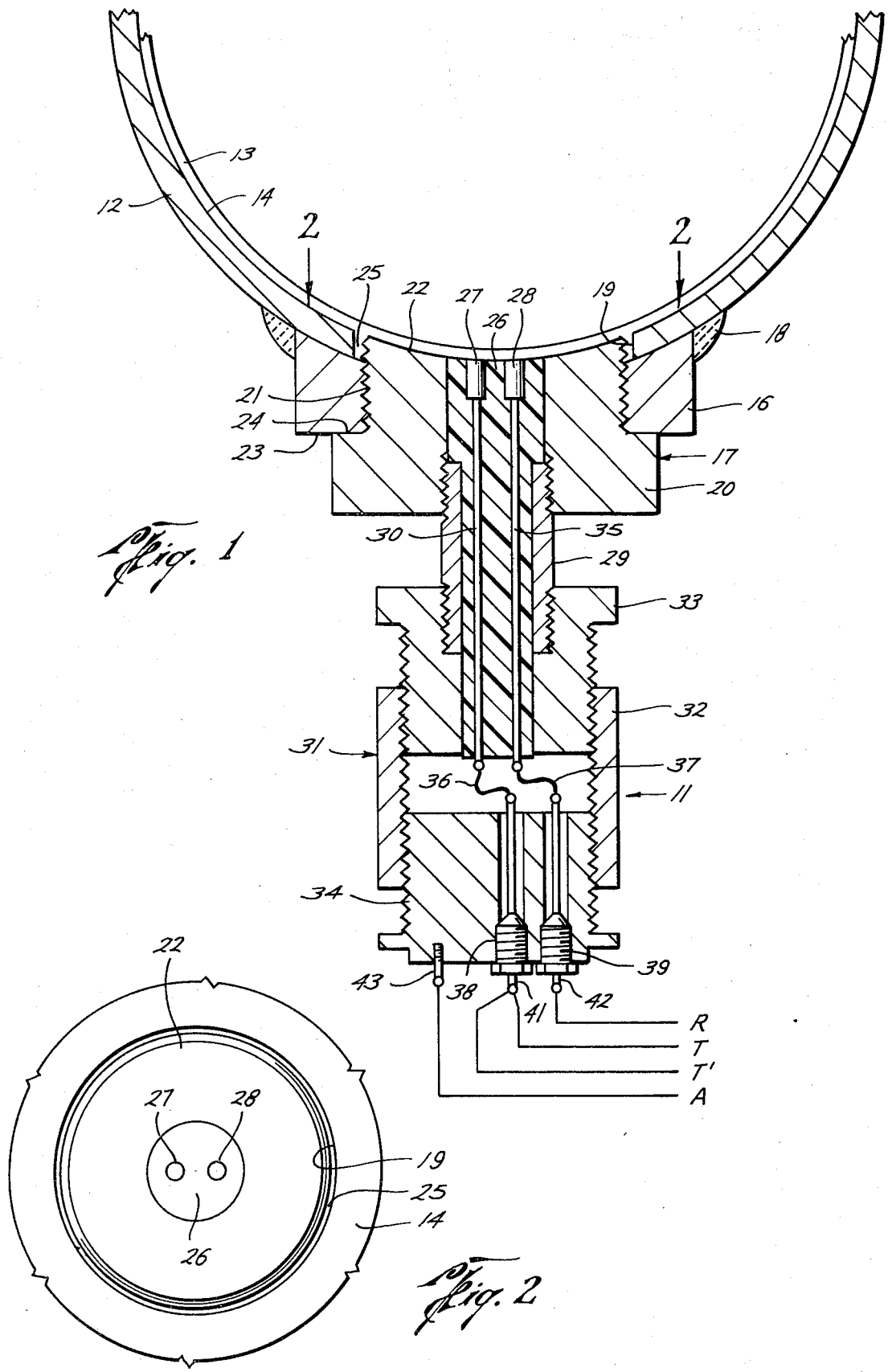

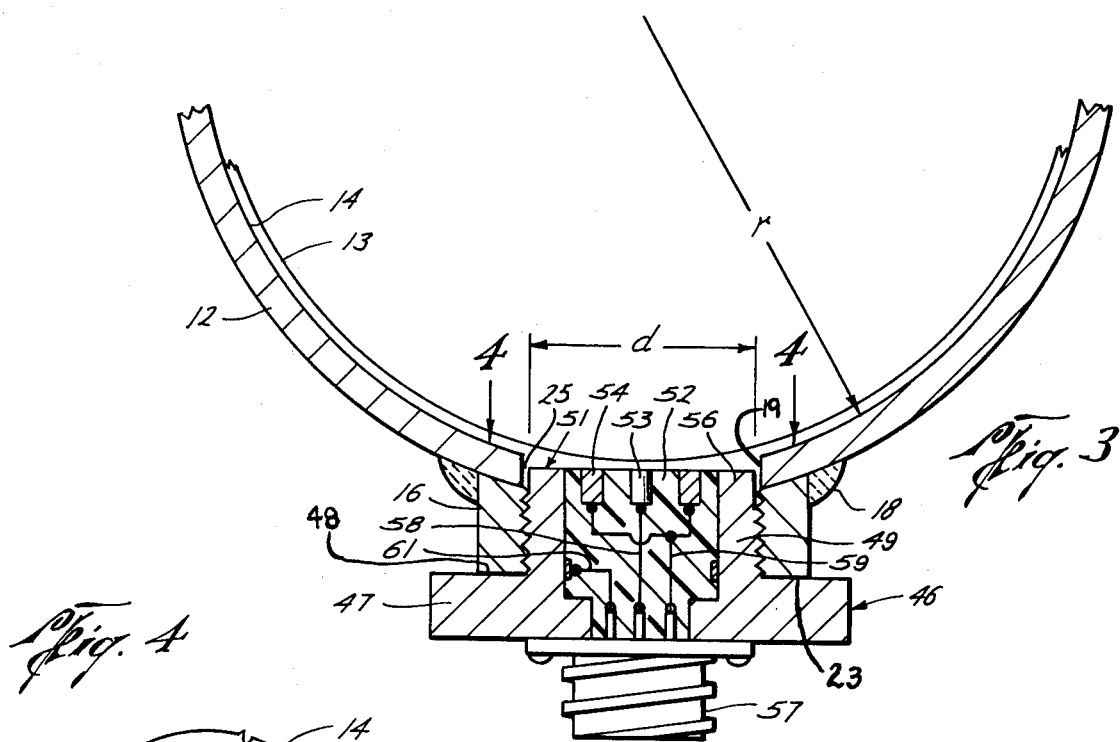

FLUSH MOUNTED CORROSION PROBE ASSEMBLY FOR PIPELINE

BACKGROUND OF THE INVENTION

1. Field of the Invention

This invention relates to measuring and testing corrosion processes, and relates particularly to the instruments and electrochemical techniques used in the study of corrosion processes.

2. Description of the Prior Art

The determination of corrosion effects within metal pipelines conducting fluids, especially those under super atmospheric pressure, is becoming important not only from the standpoint of safety but also for extending the useful life of the fluid conveying systems. Many of the pipelines are relatively small in diameter (e.g. in the range of a few inches) but many gas interstate transmission lines are as large as 48 inches in diameter. These pipelines conduct fluids under pressures which range from less than a hundred psi to as high as 1400 psi from gas field production wells. The monitoring and prevention of corrosion effects in the nearly million miles of pipeline throughout the United States is relatively expensive and difficult. However, governmental bodies now are requiring adequate and reliable monitoring programs.

In certain pipelines, corrosion monitoring is a problem since the principal region of corrosion attack exists not within the bulk of the fluids carried within the pipeline but rather within a thin boundary liquid film which is disposed upon the interior sidewall surface of the pipeline. This film may be circumferential and extend over great lengths of the pipeline. However, the film may not cover the entire circumference of the interior sidewall and may be discontinuous or extend for only short lengths along the pipeline. Alternatively, a pipeline may have a film covering only the lower portion of the interior sidewall surface and discontinuously and periodic through any substantial length. Thus, corrosion monitoring of the film represents a severe problem since the film may not exist circumferentially, or continuously with time or pipeline length, but while present, it can be a highly active corrodent causing corrosion effects with severe pitting. Many corrosion monitoring devices have been proposed for determining the corrosion occurring within pipelines. None of the known corrosion monitoring systems, as will be described hereafter, have been found practical, accurate, or reliable relative to the thin boundary liquid film.

The thin boundary liquid film in a pipeline carrying gases usually consists of an aqueous phase, or mixed phases in which the aqueous phase is continuous. Also, a pipeline completely filled with a liquid can have a thin boundary liquid film developed through concentration effects, or velocity and shear stress effects, or as a function of hydraulics. As a result, the composition of the bulk fluid within the center of the pipeline is several magnitudes less corrosive in effect than the thin boundary liquid film along the interior sidewall surface of the pipeline. This is especially true where the fluid carried within the pipeline is comprised of mixed liquid phases such as water and hydrocarbons. Many pipeline transmissions involve liquids saturated with gases such as carbon dioxide and hydrogen sulfide. The concentration effects of these gases make the thin boundary liquid film extremely locally corrosive towards pitting of interior sidewall surface of the pipeline. Under these circumstances, when an aqueous boundary liquid film contacts the pipe wall it is corroded. When no aqueous boundary liquid film exists corrosion ceases.

Known monitoring techniques which are capable of determining corrosion effects by fluids close to the interior sidewall surface of a pipeline may be divided into two general catagories. Disc-like coupons can be installed along the interior sidewall surface of the pipeline. The mounting arrangement of these coupons produces a discontinuity in the smooth sidewall of surface of the pipeline which disrupts the thin boundary liquid film which prevents an accurate determination of the corrosion effect, especially pitting. In addition, all coupon-like devices are long-term, direct measurement techniques. Thus, the intermittent presence of the thin boundary liquid film along the interior sidewall surface of a pipeline gives an indication over a long period of time that no corrosion effects existed. In actuality, the thin boundary liquid film, when it is present, creates very severe corrosion effects by pitting. For example, a high pressure gas pipeline was monitored using corrosion coupons that indicated over a 6 month period a corrosion attack that produced a coupon weight loss of only 3.86 milligrams. This weight loss correlated in the one inch square coupon to a corrosion rate of 0.06 mpy (mils per year). This pipeline was known to be covered with the thin liquid boundary film along its entire sidewall surface for only short periods of time. The actual failures of the pipeline indicated pitting in the range of 100 to 200 mpy which caused leaks in the operating interval of three to five years. Actual measurements in this pipeline by the Flush Mounted Probe Assembly of the present invention reflected that the thin boundary liquid film was present only approximately 2% of the time and produced an averaged long term corrosion rate reading of 3 mpy. However, instantaneous measurements with the Flush Mounted Probe Assembly during the presence of the film provided a readout of localized or pitting type of corrosion attack at rates of from 500 to 1400 mpy. Fortunately, inhibitors could be applied to reduce these corrosion rates by the same percentage as they do general corrosion and the effects in the pipeline were reduced by 90% so that the average long term measurement of corrosion through extended periods of time was 0.3 mpy, with a short period corrosion attack, as pitting, of 3 to 15 mpy as determined with the Flush Mounted Probe Assembly of the present invention.

Another technique for determining the effects of corrosion along the interior sidewall surface of the pipeline involves a flatsurfaced electrode or resistance wire, such as shown in U.S. Pat. No. 3,124,771. The flat resistance wire can be placed adjacent the interior sidewall surface of the pipeline. Then, the corrosion effects are determined by conventional resistance wire bridge-type instrumentation provides neither. As is well-known, resistance wire instrumentation instantaneous nor sensitive monitoring of corrosion effects. Such instrumentation involves a long term measurement of large changes in resistance produced by corrosion upon a sensing wire electrode surface. Thus, the resistance wire instrumentation, like the coupon, cannot measure the instantaneous presence of the rate of corrosion attack in the intermittent thin boundary liquid film which passes along the interior sidewall surface of a pipeline. No recognition was made in priorly used probe designs of the need to avoid introducing a surface discontinuity in the pipeline that disrupts the thin boundary liquid film present along the interior sidewall surface of the pipeline. The film usually has a thickness not over about 30 mils and is very fragile being, easily disrupted when the film is forming as under generating flow conditions. The surface discontinuity can be a protuberance or a crevice that induces sufficient macroscopic fluctuations in laminar flow to create turbulence sufficient to disrupt the film. In addition, no attempt was made to provide the electrode surfaces with a geometry and placement in a precise aligned relationship with the interior sidewall surface of the pipeline so that the thin boundary liquid film could be monitored directly.

The Flush Mounted Probe Assembly of the present invention provides both instantaneous and long term measurements of corrosion effect within the thin boundary liquid film disposed along the interior sidewall surface of a pipeline and is compatible with accepted electrochemical measurement instrumentation. Various types of polarization resistance type instrumentation may be employed but it is preferred to employ corrosion ratemeters such as are available commercially as Petrolite Instruments.

It is preferred for rapid and accurate results to measure the corrosion phenomena within a pipeline by employing electrochemical effects upon metal electrodes of a probe assembly positioned within the pipeline. An electrochemical process and apparatus especially useful in measuring corrosion rate is described in U.S. Pat. No. 3,406,101. In this technique, there is employed a corrosion ratemeter which includes a probe having three metal electrodes adapted to be exposed to a corrosive liquid. The instrumentation includes an adjustable current source, an ammeter, and a high impedance voltmeter as the primary components. The adjustable current source applies a small electric current between a "test" electrode and an "auxiliary" electrode. At the same time, the voltmeter monitors the induced polarization potential between the test electrode and a "reference" electrode. The current flow slightly polarizes the surface of the test electrode, and as a result, causes a shift in the potential between the test and reference electrodes. The current flow required to produce about 10 millivolts polarization is directly proportional to the corrosion rate of the test electrode undergoing corrosion.

One corrosion ratemeter employing the electrochemical technique which has found wide industrial acceptance is shown in U.S. Pat. No. 3,766,042. This corrosion ratemeter is portable and provides accurate instantaneous or long-term measurements of corrosion in conjunction with a probe having three metallic electrodes. Other corrosion ratemeters of similar manufacture for making corrosion measurements may be employed. It would be advantageous to employ these corrosion ratemeters with the present novel probe assembly for monitoring directly the corrosion occurring in corrodents residing in a high pressure gas environment within a pipeline. The Flush Mounted Probe Assembly of the present invention provides these results. This probe assembly permits the ready, leakproof and positive introduction of a multielectrode probe into the pipeline to be monitored in such a manner that the electrodes are precisely aligned in a contoured and diminsioned smooth end face at a selected relationship to the inner sidewall surface of the pipeline and the thin boundary liquid film is not disrupted. Normal operation of the pipeline is not disturbed. In addition, the probe is replaceably mounted within the pipeline and a fluid-tight seal is produced so that no pipeline fluids can leak past the probe. Other advantageous results obtained with the present probe assembly will be appreciated from the following discussion.

SUMMARY OF THE INVENTION

In accordance with this invention, a flush mounted probe assembly is provided for monitoring the corrosion environment within a thin boundary liquid film disposed along the interior sidewall surface of a pipeline carrying fluids. This assembly comprises a nipple means secured to the pipeline and having an axial opening therethrough aligned with an opening within the sidewall of the pipeline. Probe means, received within the nipple means, are formed by a metal member having an end portion adapted to project relatively snugly into the opening and terminating in an end face residing in substantial alignment with the interior sidewall surface of the pipeline. Means are associated with the nipple means for releasably securing the probe means against unintentional displacement from the nipple means by fluid pressure within the pipeline. Means are associated with the nipple means for sealing the probe means in a fluid-tight relationship within the nipple means. The end face of the probe means has an imperforate smooth surface exposed to pipeline fluids. Also, the end face is contoured and dimensioned within the opening to substantially conform to the interior sidewall surface of the pipeline without any surface discontinuity which can disrupt the thin boundary liquid film disposed along the interior sidewall surface of the pipeline. Electrode means are carried by the probe means within the end face. The electrode means have smooth exposed surfaces merging into the smooth surface of the end face. Electrical conductor means are connected to the electrode means and are carried by the probe means. These conductor means extend in electrical isolation from the probe means to form an external circuit connection.

DESCRIPTION OF THE DRAWINGS

FIG. 1 is a side elevational view (partially in section) showing the Flush Mounted Probe Assembly of the present invention mounted for monitoring the corrosion environment within a pipeline;

FIG. 2 is a plan view taken from the interior of the pipeline of the probe assembly shown in FIG. 1;

FIG. 3 is a side elevational view (partially in section) showing another embodiment of the Flush Mounted Probe Assembly of the present invention having annular electrodes for monitoring the corrosion environment within a pipeline;

FIG. 4 is a plan view from the interior of the pipeline of the probe assembly shown in FIG. 3;

FIG. 5 is a graph illustrating corrosion rate measurement versus thickness of liquid covering the face of the probe of FIGS. 3 and 4; and FIG. 6 is a pictorial representation of the probe structure providing data for the graph of FIG. 5.

DESCRIPTION OF SPECIFIC EMBODIMENTS

Referring now to FIG. 1, a Flush Mounted Probe Assembly 11 of the present invention is shown secured to a pipeline 12 for monitoring the corrosivity of a thin boundary liquid film 13 disposed along the interior sidewall surface 14 of the pipeline 12 carrying fluids.

The pipeline 12 is usually constructed of a ferrous metal and carries fluids such as natural gas, crude oil and various types of aqueous or partially aqueous liquids. The film 13 can be of an aqueous liquid phase, or a mixture of aqueous and immiscible phases, and the film can include various suspended solids such as sand. The film 13 with a thickness of between 5 and 30 thousandths of an inch is common in natural gas pipelines. In addition, the film 13 may be continuous or discontinuous throughout the interior circumference, and length of the pipeline 12 but it could also reside only in the lower portion thereof, as is shown in FIG. 1. In addition, the film 13 can be present only intermittently, as for example, about 2 percent of the time a pipeline is in operation.

The probe assembly is comprised of a mounting adapter on the pipeline and a removably mounted probe positioned in an opening extending through the adapter and sidewall of the pipeline.

In one embodiment, the probe assembly 11 is comprised of a nipple 16 in which is mounted a probe 17. The nipple 16 is secured to the pipeline 12 by a weld 18 where these components are ferrous metals. An opening 19 is provided within the pipeline 12 in alignment with the axial opening through the nipple 16. Usually, the opening 19 will be circular in cross-section. Preferably, the nipple 16 is mounted with its axial opening substantially perpendiculaar to the longitudinal axis of the pipeline 12.

The probe 17 may be of any suitable construction which satisfies the needs of the present invention. For example, the probe 17 is constructed of a pipe plug 20 carrying a threaded end portion 21 which is received within the threaded interior surface of the nipple 16, and the end portion 21 preferably has a substantially cylindrical configuration. The threaded end portion 21 of the probe 17 is dimensioned to project relatively snugly into the opening 19 of the pipeline 12, leaving only a very small annulus 25 open to pipeline fluids between these parts. Specifically, the crevice-like annulus 25 should have a thickness and depth of only the smallest dimensions so that pipeline fluids can fill this "crevice" but yet cannot circulate through it so as to create a surface discontinuity to disrupt the film 13. For example, annulus 25 can be about 0.003 inches in thickness and about 0.60 inches in depth for purposes of producing non-circulation or stagnation of the trapped pipeline fluids.

The threaded end portion 21 terminates in an end face 22 which is in substantial alignment with the interior sidewall surface 14 of the pipeline 12. More particularly, the end face 22 is formed of an imperforate smooth surface which is contoured to substantially conform to the interior sidewall surface 14 without a surface discontinuity to disrupt the film 13. For improved results, the end face 22 is contoured into a semi-cylindrical configuration with a radius of curvature to conform exactly with the radius of the interior sidewall surface 14 of the pipeline 12. Stated in another manner, the end face 22 is a concave surface relative to the interior of the pipeline 12. Although there may be a slight variation in the contour of the smooth surface of the end face 22 relative to surface 14, it should not be of a semicylindrical configuration having a lesser radius of curvature than the radius of the surface 14 of the pipeline 12. Under these circumstances the peripheral edges of the end face 22 adjacent the opening 19 will not protrude to form a surface discontinuity within the pipeline 12 to disrupt the film 13. Stated in another manner, the contour of the smooth surface of the end face 22, when of a semicylindrical configuration, should be at a radius equal to or greater than the radius of the interior sidewall surface 14. As will be apparent from the drawings, the end face 22, when of a semicylindrical configuration, can be coaxial with the longitudinal axis of the pipeline 12.

The smooth surface of the end face 22 contoured into a semicylindrical configuration conforms with the interior sidewall surface 14 of the pipeline 12. Therefore, the end face 22 can be dimensioned into any practical length and width relative to the radius of the surface 14 of the pipeline 12. The only limitation is the practical construction of the probe and nipple secured to the pipeline 14. As a result, the imperforate smooth of the end face 22 in a semicylindrical configuration avoids any surface discontinuity to disrupt the thin boundary liquid film 13.

The probe 17 and nipple 16 cooperate so that the end portion 21 is inserted to the proper dimension of projection into the opening 19, with the semicylindrical configuration of the end face 22 aligned with the surface 14 of the pipeline 12. For this purpose, the threaded portion 21 of the probe 17 extends axially from a flat end 23 formed on the nipple 16 to the interior sidewall surface 14 of the pipeline 12. The probe 17 carries the usual polygonal surfaces on plug 20 for engagement by a wrench or the like and has a transverse flat shoulder 24 adjacent the threaded portion 21. The flat shoulder 24 engages at least a portion of the end face 23 on the nipple 16 and the end face 22 is placed precisely with its smooth surface in substantial conformity with the interior sidewall surface 14. If desired, a very thin gasket or other fluid seal may be accomodated between the nipple's end face 23 and the plug's flat shoulder 24. Alternatively, a sealing compound placed on the engaging threads of the nipple 16 and probe 17 provides a fluid seal between the nipple 16 and the probe 17. As the result, the probe 17 is received within the nipple 16 in a fluid tight relationship and held securely against displacement by fluid pressures within the pipeline 12.

The probe 17 at the end face 22 carries electrodes for monitoring the corrosivity of the film 13 in the pipeline 12 by suitable electrochemical techniques such as described in U.S. Pat. No. 2,766,042. These electrodes can be of any suitable geometry and construction. However, the electrodes must have imperforate smooth exposed surfaces merging into and becoming a part of the smooth surface of the end face 22. The electrodes usually are a metallic material such as 1020 mild steel. Preferably, three electrodes are provided in the probe 17 with two electrodes insulated from one another and the probe 17, and the metal plug 20 forming the third electrode. However, the probe 17 may carry three electrodes in an electrically isolated relationship relative to the metal plug 20.

In one embodiment, the probe 17 has a central insulator 26 which is mounted coaxially within the plug 20. The insulator 26 merges into and becomes a part of the smooth surface of the end face 22. Electrodes 27 and 28 are mounted within the insulator 26. These electrodes are formed by steel rods embedded within the insulator 26 and have smooth end surfaces conforming to the smooth surface of the end face 22. The metal plug 20 encircling the insulator 26 forms the third electrode of the probe assembly 11 for purposes of the present invention.

The plug 20 connects to a tubular extension for convenience in providing exterior terminals connectible to external circuitry for the corrosion measurement determination. For this purpose, the plug 20 receives a nipple 29 which connects to a terminal adapter 31. The adapter 31 is comprised of a collar 32 mounting bushings 33 and 34 in a fluid-tight relationship. The insulator 26 extends through the nipple 29 and bushing 33, and terminates at the open interior of the collar 32. Electrical conductors 30 and 35 extend from the electrodes 27 and 28 into the insulator 26 and connect by leads 36 an 37 to feedthrough terminals 38 and 39 having external terminal pins 41 and 42, respectively. A third terminal 43 in the bushing 34 provides electrical continuity to the metal plug 20.

With reference to the instrumentation in U.S. Pat. No. 3,766,042, the terminals 41, 42, and 43 connect in an external circuit by flexible conductors identified as R, T, T', and A. With this arrangement, the electrode 28 performs the reference electrode function (and connects to lead R), the electrode 27 performs the test electrode function (and is connected to leads T and T' jointly), and the metal plug 20 connects to the lead A and performs the auxiliary or current electrode function. With this described arrangement of instrumentation, the corrosivity of the film 13 can be determined by use of the probe assembly 11.

Referring momentarily to FIG. 2, the insulator 26 resides centrally within the end face 22. The electrodes 27 and 28 are spaced symmetrically within the insulator 26. These electrodes are shown as having a circular configuration. However, these electrodes can have other configurations such as rectangular and irregular forms but will operate satisfactorily in most applications of corrosion monitoring.

Good results are obtained whenever the resistivity of the film 13 covering the electrodes of the probe 17 is of a reasonable value. It will be appreciated that applied current flow between the metal plug 20 (as the auxiliary electrode) and the test electrode 27 creates a polarization of the test electrode 27 relative to the reference electrode 28. This polarization, usually approximately 10 millivolts, makes the applied current flow a measure of the corrosion effect of the film 13 covering the electrodes. In certain situations relative to fluids in the pipeline 12, and in particular to the film 13, the ionic content of the fluid becomes very low so that its resistivity becomes very high by magnitudes of change to extreme levels of 500,000 OHMS/centimeters. Under these conditions for a 10 mv applied potential, the three dimensional current field becomes very diverse and could be intercepted by the reference electrode. If the reference electrode intercepts a line of current, IR type potential error in the measurement (up to several hundred percent) would be created since the reference electrode 28 (and the instrumentation connected thereto) cannot distinguish between the 10 mv polarization potential developed at the test electrode 27 and the resistance-induced potential developed by the current flow through the electrolyte immediately adjacent to the reference electrode 28. It was discovered experimentally that the IR potential error induced at the reference electrode 28 by applied current flow is dependent upon the resistivity of the fluid and electrode geometry and not the 10 mv polarization of the test electrode 27. The reference electrode 28 sees the algebraic sum of potentials and this summation magnitude changes as a certain function of the resistivity of the fluid covering the electrodes in a given special regime.

In accordance with other novel features of the present invention, a particlar unique geometry and configuration has been discovered for the electrodes of the Flush Mounted Probe Assembly to reduce geometrically the magnitude of IR type potential errors associated with known electrode arrangements. A unique embodiment of this novel electrode arrangement is illustrated in FIG. 3.

In FIG. 3 there is shown an embodiment of the present Flush Mounted Probe Assembly 46 having a unique configuration of electrodes to reduce the magnitude IR potential type errors created by increasing resistivity of fluids. In FIG. 3, like elements carry like numerals relative to the probe assembly structures shown in FIG. 1 to simplify the description. Threadedly received within the nipple 16 is a probe 46. The probe 46 is secured in precise position within the nipple by a shoulder 48 engaging the end face 23 so as to limit the projection of a cylindrical end portion 49 into the opening 19 within the pipeline 12. The threaded end portion 49 of the probe 17 terminates in an imperforate smooth end face 51 which is transverse to the longitudinal axis of the cylindrical end portion 49. The end face 51 may be semicylindrical as was described for the probe 17 relative to FIGS. 1 and 2. Preferably, the end face 51 is flat or planar in configuration and does not require orientation relative to the longitudinal axis of the pipeline 12. An insulator 52 is mounted centrally within the end portion 49 and carries a plurality of concentrically arranged electrodes. These electrodes can include a central electrode 53 and one or more annular electrodes 54 and 56. Although a second annular electrode may be disposed in the insulator 52 encircling the first annular electrode 54, the metal plug 47 of the probe 46 can provide the second annular electrode 56. The electrodes have an imperforate smooth surface that merge into the end face 51 without any surface discontinuity to disrupt the film 13. The surface of these electrodes will be planar when the end face 51 is planar in configuration.

Referring momentarily to FIG. 4, preferably, the central electrode 53 is circular in configuration and annular electrodes 54 and 56 are disposed concentrically thereabout in spaced apart relationship within the insulator 52. The insulator 52 is of a suitable material. Preferably, the insulator 52 is a glass-filled epoxy that is physically strong, has good insulative properties and can resist chemically most fluids commonly encountered within pipeline service. The electrodes are formed of a suitable material and can be fabricated from a 1020 steel.

The electrodes 53 and 56 usually provide the reference and auxiliary electrode functions, respectively, while the electrode 54 provides the test electrode function. Although the functions of the electrodes 53 and 56 can be interchanged, it is preferred to have the electrode 53 perform the reference electrode function.

A conventional multipin AN connector 57 is carried exteriorly upon the plug 47 and is interconnected with the electrodes by conductors 58, 59, and 61. These conductors are embedded within the insulator 52 by conventional manufacturing techniques.

The described arrangement of the concentrically arranged. annular electrodes within the end face 51 provides an unexpected and unique result relative to changes in resistivity of the fluid contacted by the probe 46. It is belived that this novel result is provided by the symmetry in spacial arrangement of the electrodes. It has been found that this particular arrangement of concentric disposed electrodes within the end face 51 provides a reduction in the error due to the IR potential drop created adjacent the reference electrode 53 by applied current flow between the test and auxiliary electrodes 54 and 56 as the resistivity of the fluid contacted by the probe increases. For example, each equal increase in resistivity of the fluid produces only a fixed fractional increase in the error in the corrosion magnitude reading. As will be recalled from the previous description of the embodiment relative to FIGS. 1 and 2, each equal change in resistivity produced at least a magnitude change in the error in the corrosion reading.

One explanation for the novel results in a probe with these concentrically arranged, annular electrodes resides in the lines of force and their direction of current flows within isotropic media. Referring briefly to FIG. 4, applied current flows between the auxiliary electrode 56 to the test electrode 54 to produce lines of force (in vertical planes) which loop radially about a center of revolution which is the reference electrode 53. Since these lines of force all have the same magnitude of current flow, and are exactly opposing one another across the reference electrode 53, the IR type of potential induced adjacent the reference electrode 53 is minimal. There is no probability that the reference electrode will intercept a line of current.

If the reference and auxiliary electrodes were reversed, i.e., the current flow would be between the test electrode 54 and auxiliary electrode 53. The lines of force (in vertical planes) are produced which loop radially about a center of which is now the auxiliary electrode 53. If a potential error is to be produced then a line of current must lie exactly in the probe face plane having no curvature whatever. This will cause the total current line length to approach infinity. Because the magnitude of error is given by $V_{error} = (l/l_{total})V_{total}$ (where $l$ = length between reference and test electrodes, $l_{total}$ = total length of current line, $V_{total}$ = potential applied between test and auxiliary electrodes), $V_{error}$ must go to zero since $V_{error} = (l/\infty) \times V_{total} = 0$.

Comparative corrosion data were obtained for the case of several probe configurations I–V exposed to three electrolytes: deionized water, glacial acetic acid and 10% salt solution, having solution conductivities ranging from 0.02 $\mu$ mhos to around 100,000 $\mu$ mhos. These data are shown in Table 1. In the case where the probes were exposed to 10% sodium chloride solution which has a solution conductivity around 100,000 $\mu$ mhos, complete agreement (within the limits of the polarization resistance technique) was obtained. A significant disagreement was observed when the probes were exposed to deionized water having conductivity of 2 $\mu$ mhos. Finally, glacial acetic acid having a conductivity of 0.02 mhos, produced a disagreement of two orders of magnitude (100 times lower than with probe types I & II). The data given in Table 1 illustrates that the magnitude of the disagreement in corrosion rates as measured by the different probes in each increases severely in solutions of very low conductivity. As may be seen from the following, the centric annular electrodes of probe types I and II were proven to be greatly superior to the other probe types. However, in the usually encountered solutions of the high conductivity variety (salt solution) all probe types gave acceptable results.

TABLE I

Probe type vs Average Corrosion Rate (CR) in Various Electrolytes (Electr.)

| Probe type | Electr. | CR | Electr. | CR | Electr. | CR |
|---|---|---|---|---|---|---|
| I | deionized water | 9 | Acetic acid | & 2.1 | 10% Salt Sol. | 40 |
| II | '' | 9 | '' | 1.6 | '' | — |
| III | '' | .2 | '' | .02 | '' | 20 |
| IV | '' | .5 | '' | .03 | '' | 35 |
| V | '' | .5 | '' | .04 | '' | 25 |

Average Corrosion Rate CR in mpy's
I       Probe embodiment FIGS. 3 & 4, electrode 53 as reference.
II     Probe embodiment FIGS. 3 & 4, electrode 56 as reference.
III    Probe embodiment FIGS. 1 & 2
IV    Probe of U.S. 3,558,462 with 3-inline electrodes
V     Probe of U.S. 3,632,495 with 3-triangular disposed electrodes.

Corrosion measurements were made in a gas gathering system having multi-phase flow conditions. The measurements were made using probe type IV located in a "drip pot", and using the probe type I as listed in Table I. The probe type IV measurements were two orders of magnitude lower than the probe type I corrosion rate readings, which more closely reflected actual system failures. The low readings by the probe type IV are due in part to depletion of corrodent in the vicinity of the electrodes since the corrodent molecules had to diffuse through a long distance (3 to 6 inches) before reaching the liquid surface. The drip pot was provided by a depression in the lower portion of a pipe line which collected sufficient liquid to cover the rod electrodes of probe type IV to a depth of several inches. The probe type I was mounted substantially aligned with the interior sidewall surface of the pipeline and covered by a thin film of the liquid. The probe type IV gave a general corrosion rate measurement of 0.5 mpy which predicts a failure in 500 years. The probe type I of the present invention gave a general corrosion rate measurement of 50 mpy which predicts a failure in 5 years. Actual experience on the pipeline shows a failure to occur in one year at the established corrosion environment, which is produced by pitting conditions and not solely upon general corrosion attack.

The end face 51 of the probe 46 may have its smooth surface contoured into a semicylindrical configuration in conformity with or greater than the radius r of the interior sidewall surface 14 of the pipeline 12. However, it has also been found unexpectedly that the end face 51 can be planar or substantially planar and carried transversely to the longitudinal axis of the probe 46 if certain dimensional parameters are observed. When the end face 51 is planar, the dimensions of the end portion 49, within the opening 19, become significant relative to the radius $r$ of the surface 14. For example, the end portion 49 is cylindrical and has a diameter $d$ as indicated in FIG. 3. The end face 51 obviously does not project into the film 13 to become a surface discontinuity for disrupting this film 13. However, the peripheral edge of the end portion 49 is covered by a greater thickness of the film 13 then that portion of the probe 47 immediately adjacent the electrode 53. Depletion of the corrodent in the peripheral thickness of film occur if the crevice depth were not limited. This corrodent depletion is avoided by limiting this film thickness $s$ according to a certain structural relationship between the radius $r$ and the diameter $d$ of the end portion 49 with reference to FIG. 6.

It has been found that superior and accurate results are obtained with the probe 46 when the end face 51 and end portion 49 is planar and circular with a diameter $d$ and related to the radius $r$ of the interior sidewall surface 14 by the formula; $r \geq 1.25\ (d)^2$, the dimensions being in inches. This relationship between the contour and dimensions of the end face 51, and radius $r$ of surface 14 is indicated by the following experimental data.

There is a relationship between the peripheral thickness $s$ of the depth at crevice 25 to the surface of end face 51 and the accuracy with which corrosion measurements can be made in the film 13 having a thickness of 5–30 mils. If the thickness $s$ is above a certain magnitude then the liquid has a depth where diffusion and disturbance effect the accuracy of corrosion measurements.

Laboratory data was taken with the probe 46 set below the interior surface 14 in ranging thickness of $s$. These data are shown graphically in FIG. 5 of the drawings and illustrate the limiting diffusion effects on corrosion rate versus thickness of film 13. The actual corrosion rate, i.e., when $s=0$, is about 14 mpy. Thus, a 50 percent error in corrosion rate measurement exists when the thickness $s$ is 100 mils, and 85 percent error when the thickness $s$ is 5000 mils. Thus, the thickness $s$ sets the preferred relationship between $r$ and $d$ of probe 46.

Mathematically, the preferred relationship is devised as follows from the right triangle shown in FIG. 6 of the drawings:
1. $(r)^2 + (d/2)^2 = (r+s)^2$; which equals;
2. $r^2 + 2rs + s^2$;
3. since $s$ is much less than $r$ and also $2rs$, then $(s)^2$ can be taken as zero;
4. therefore, $r^2 + 2rs = r^2 + (d/2)^2$;
5. since the 100 mil (0.1 inch) thickness for $s$ is at the inflection of the curve for accurate measurements of corrosion rate, then $s \leq 0.1$ inch $\leq d/8r^2$; which gives
6. $r \geq 1.25\ (d)^2$ in the preferred embodiment of probe 46.

As will be apparent, the concentrically disposed annular metal electrodes in the probe 46 may be placed into end surface 51 which is contoured either in a semicylindrical, planar, or other contour to conform to the surface 14 as long as there is no surface discontinuity created to disrupt the film 13 disposed along the interior sidewall surface 14 of the pipeline 12. In addition, the central electrode 53 could be an annular structure as are electrodes 54 and 56 and all the electrodes are mounted concentrically within the insulator 52. An annulus 25 between the probe 46 and the opening 19 exists in the pipeline 12. This annulus 25 should be small relative to the diameter $d$ of the end face 51. In other words, the end portion 49 of the probe 47 should fit snugly into the opening 19. As a result, film 13 fills such annulus 25 but becomes a static body if the thickness $s$ is allowed to become greater than that value set by the condition $r \geq 1.25\ (d)^2$.

The best utility of the probes 17 and 46 is in determining the corrosion effects within a film 13 having a small thickness. However, the film 13 may have appreciable depth. For example, the pipeline 12 may be filled with liquid which is under static flow conditions and can be considered to be a container. With time, diffusion effects produce a considerable depth in the film 13 and in essence, the measurement will be representative of the corrosion effects within the body of liquid itself. Also, the pipeline 12 may be noncircular in cross section. In this instance, the end face of the probe will be contoured and dimensioned to conform with whatever surface is to be monitored for corrosion problems.

It will be apparent from the foregoing that there has been described herein a Flush Mounted Probe Assembly which can be placed into a pipeline to provide instantaneous and long term readings of the corrosion effects occurring in fluids immediately adjacent the inner sidewall surface of a pipeline and without disrupting the thin films of fluid disposed along such interior sidewall surface of the pipeline. In addition, a unique arrangement of concentrically arranged, annular electrodes has been described which overcomes IR potential type errors created upon increases in resistivity of the fluid subject to corrosion determinations. The electrodes of the probe may be any suitable metallic material but usually will be made of ferrous metals. It is envisioned that changes can be made to the construction of the probe while following the teachings of the present description to obtain the desired results without having to reproduce identically the structures heretofore described.

Various modifications and alterations in the described Flush Mounted Probe Assembly will be apparent to those skilled in the art from the foregoing description which do not depart from the spirit of the invention. For this reason, these changes are desired to be included within the scope of the appended claims. The appended claims define the present invention; the foregoing description is employed for setting forth the present embodiments as illustrated and is not limitative in nature.

What is claimed is:
1. A flush mounted probe assembly for monitoring the corrosion environment within a thin boundary liquid film disposed along the interior sidewall surface of a pipeline carrying fluids comprising:
   a. nipple means secured to a cylindrical pipeline having an internal radius $r$, and said nipple having an axial cylindrical opening therethrough aligned with a circular cross-sectioned opening within the sidewall of said pipeline;
   b. probe means comprising a metal member with a circular cross-section received within said nipple means, and said probe means projecting snugly into said opening in said sidewall and terminating in an end face residing in substantial alignment with the interior sidewall surface of said pipeline;
   c. means for releasably securing said probe means within said nipple means;

d. means for sealing said probe means and nipple means into a fluid-tight relationship;

e. said end face having a circular cross-section exposed to pipeline fluids with a substantially smooth imperforate surface selected from a planar surface disposed transversely to the longitudinal axis of said metal member of said probe means, or a semi-cylindrical smooth concave surface aligned with the axis of said pipeline and having a radius of curvature not less than the radius r of said pipeline;

f. said end face is circular in cross-section with a diameter d and related to the internal radius $r$ of said pipeline by the formula: $r \geq 1.25(d)^2$ where in the formula the terms $r$ and $d$ are dimensioned in inches, whereby said end face is contoured and dimensioned within said opening to substantially conform to the adjacent interior sidewall surface of said pipeline without a surface discontinuity greater than 100 mils in thickness to disrupt the thin boundary liquid film disposed along the interior sidewall surface of said pipeline;

g. electrode means carried by said probe means on said end face, and said electrode means provided by a plurality of metal electrodes having smooth exposed surfaces merging with and forming in part said smooth imperforate surface on said end face, and said metal electrodes separated from one another by an insulator means carried centrally with said end face and forming a portion of said smooth imperforate surface; and h. electrical conductor means connected to said metal electrodes and carried by said probe means, and said conductor means extending in electrical isolation from said probe means to form an external circuit connection.

2. The flush mounted probe assembly of claim 1 wherein said electrode means are provided by one or more annular metal electrodes mounted concentrically about a central metal electrode in spaced apart relationship within said insulator centrally located within and forming a portion of said smooth surface on said end face.

3. The flush mounted probe assembly of claim 2 wherein the central metal electrode and an encircling annular electrode serve reference and auxiliary electrode functions, respectively, and an intervening annular electrode provides a test electrode function.

* * * * *

UNITED STATES PATENT AND TRADEMARK OFFICE
CERTIFICATE OF CORRECTION

PATENT NO. : 3,996,124
DATED : December 7, 1976
INVENTOR(S) : Paul E. Eaton and Robert R. Annand It is certified that error appears in the above-identified patent and that said Letters Patent are hereby corrected as shown below:

Column 1, line 51, "film.." should be changed to
--- film. ---

Column 2, line 1, "of interior" should read
--- of the interior ---

Column 2, line 52, "flatsurfaced" should read
--- flat-surfaced ---

Column 2, line 57, "provides neither" should be deleted.

Column 2, line 58, after "instrumentation" there should be inserted
--- provides neither ---

Column 3, line 4, "fragile being," should be changed to
--- fragile, being ---

Column 5, line 28, "perpendiculaar" should read
--- perpendicular ---

Column 6, line 16, "smooth" should read
--- smooth surface ---

UNITED STATES PATENT AND TRADEMARK OFFICE
CERTIFICATE OF CORRECTION

PATENT NO. : 3,996,124
DATED : December 7, 1976
INVENTOR(S) : Paul E. Eaton and Robert R. Annand It is certified that error appears in the above-identified patent and that said Letters Patent are hereby corrected as shown below:

Column 10, line 7, "0.02 mhos" should read
--- 0.02μ mhos ---

Column 10, line 11, after "each" there should be inserted
--- electrolyte ---

Column 10, line 13, "centric" should read
--- concentric ---

Columns 9 and 10, in TABLE 1, in 5th column thereof,
" &" should be deleted

Columns 9 and 10, in TABLE 1, "Average Corrosion Rate CR in mpy's" should read
--- (Average Corrosion Rate CR in mpy's) ---

Column 11, line 12, after "film" there should be inserted
--- could ---

Column 11, line 56, "$d/8r^2$" should read
--- $d^2/8r$ ---

Signed and Sealed this

Nineteenth Day of April 1977

[SEAL]

Attest:

RUTH C. MASON
Attesting Officer

C. MARSHALL DANN
Commissioner of Patents and Trademarks